United States Patent
Park et al.

(10) Patent No.: US 8,552,871 B2
(45) Date of Patent: Oct. 8, 2013

(54) APPARATUS AND METHOD FOR SENSING PHOTOPLETHYSMOGRAM AND FALL

(75) Inventors: Chan Kyu Park, Daejeon (KR); Jae Hong Kim, Daejeon (KR); Joo Chan Sohn, Daejeon (KR); Jae Yeon Lee, Daejeon (KR); Yun Koo Chung, Daejeon (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 371 days.

(21) Appl. No.: 12/973,852

(22) Filed: Dec. 20, 2010

(65) Prior Publication Data

US 2011/0148630 A1    Jun. 23, 2011

(30) Foreign Application Priority Data

Dec. 21, 2009  (KR) .................. 10-2009-0127716

(51) Int. Cl.
*G08B 23/00* (2006.01)

(52) U.S. Cl.
USPC ................. 340/573.1; 340/540; 340/573.7

(58) Field of Classification Search
USPC ............................................ 340/540, 573.1
See application file for complete search history.

(56) References Cited

U.S. PATENT DOCUMENTS

| | | | |
|---|---|---|---|
| 2005/0038327 A1 | 2/2005 | Tanaka et al. | |
| 2009/0024007 A1 | 1/2009 | Lee et al. | |
| 2010/0298656 A1* | 11/2010 | McCombie et al. | 600/301 |
| 2010/0324384 A1* | 12/2010 | Moon et al. | 600/323 |

FOREIGN PATENT DOCUMENTS

| | | |
|---|---|---|
| KR | 1020010028953 A | 4/2001 |
| KR | 1020020028539 A | 4/2002 |
| KR | 10-2007-0014251 B1 | 2/2007 |
| KR | 10-2008-0050993 B1 | 6/2008 |
| KR | 1020090029561 A | 3/2009 |
| KR | 1020090099147 A | 9/2009 |
| WO | WO 03/096892 A1 | 11/2003 |

\* cited by examiner

*Primary Examiner* — Kerri McNally

(57) ABSTRACT

Disclosed are an apparatus and a method for sensing photoplethysmogram and fall. According to the present invention, the apparatus and for sensing photoplethysmogram and fall may include: a sensor unit that senses acceleration and photoplethysmogram; a photoplethysmogram/fall determining module that synthetically tests sensed acceleration signals and photoplethysmogram signals sensed by the sensor unit to determine whether emergency occurs due to fall or emergency occurs due to photoplethysmogram; and a communication module that transmits the test results.

20 Claims, 4 Drawing Sheets

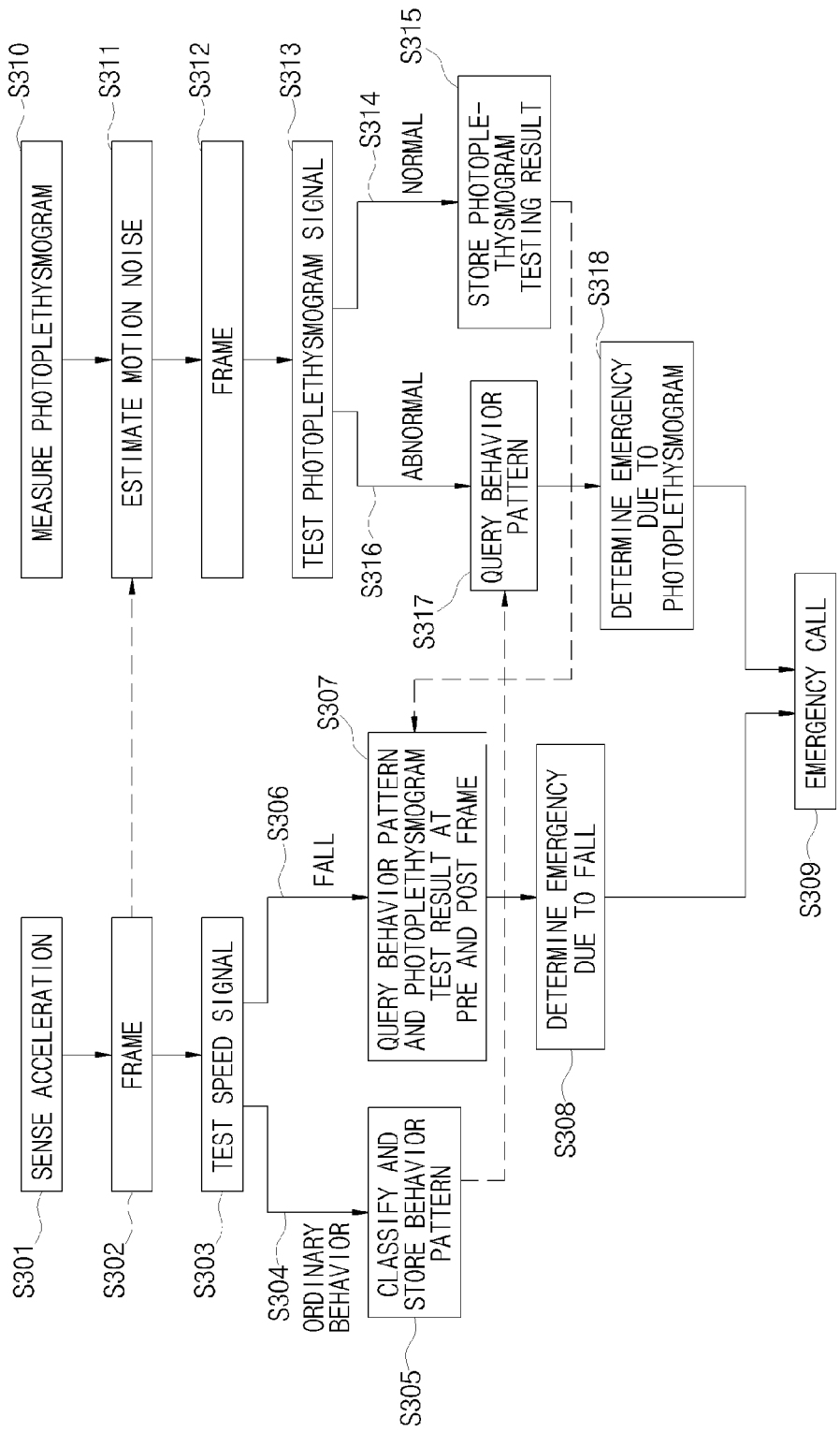

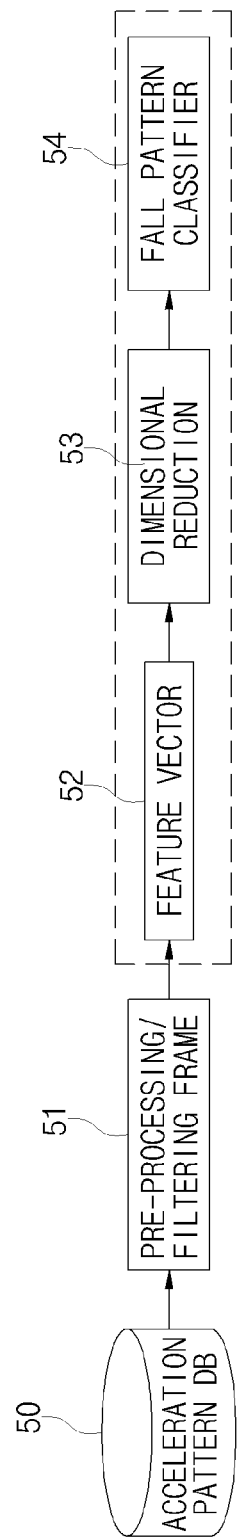

APPARATUS AND METHOD FOR SENSING PHOTOPLETHYSMOGRAM AND FALL

CROSS-REFERENCE TO RELATED APPLICATIONS

This application claims priority under 35 U.S.C. §119 to Korean Patent Application No. 10-2009-0127716, filed on Dec. 21, 2009, in the Korean Intellectual Property Office, the disclosure of which is incorporated herein by reference in its entirety.

BACKGROUND OF THE INVENTION

1. Field of the Invention

The present invention relates to a technology of observing the bio signal and behavior change of a user and determining if it is an emergency or not when an abnormal state is sensed using various sensors.

2. Description of the Related Art

As a health care technology is combined with an IT technology, an environment capable of coping with an abnormal sign is being realistically built by obtaining bio information of people with chronic diseases, the elderly, or people with specific diseases in a home, a nursing home, or a silver town by a portable measuring apparatus even though they do not enter a hospital and analyzing and determining the bio information.

Under this environment, obtaining and analyzing bio signals of the user are the just basic information, but should be implemented.

Specifically, first, it is preferable to sense reliable bio signals without restricting the user.

Second, it is preferable to form a micro apparatus so that the user can wear/carry an apparatus.

Third, it is preferable that data can be collected an online and support a wireless-based communication infrastructure as an alarm apparatus for an emergency.

An effective and reliable service cannot be provided until the conditions can be satisfied.

A photoplethysmogram signal of many bio signals is used as fundamental data providing a variety of information such as the pulse rate, oxygen saturation, heart rate variability (HRV) of the user, etc., which has been currently used as an important vital signal of a patient in a medical center. Further, the photoplethysmogram signals are sensed through the oxygen saturation apparatus, which are used to calculate the oxygen saturation and the heart rate included in blood. If the oxygen saturation and the heart rate are out of a normal range, it is informed that an emergency may occur.

In daily life, it is not easy to acquire bio signals from the user, but pulse signal, body temperature, skin conductance, blood pressure, ECG, etc., can be acquired through a wireless communication based wearable apparatus. Further, with the development of a MEMS semiconductor technology, inertial sensors are generalized, such that the behavior patterns of the elderly may be derived through the behavior information of daily life. In particular, in the case of the elderly, there have been statistics that the elderly experience a fall during a daily life several times a year. The fall causes several emergency and leads to death.

Unlike the sensing of bio signals that are relatively hard to achieve during movement, a fall sensing technology develops a system that wears a small-sized apparatus on the waist or chest or as a necklace type, senses a fall using an MEMS inertial sensor when the fall occurs, and transmits emergency information. However, a false positive case that determines to be the fall even though the fall does not occur frequently occurs. In this case, there are problems in that time manpower is unnecessarily wasted due to a false report. In addition, due to the false negative that determines not to be the fall even though the fall occurs, if the elderly subjected to the fall do not recover themselves, there is a problem in that they are in an emergency situation. Therefore, in addition to the inertial sensor, additional information to improve reliability for the fall determination is currently needed.

In the case of health care targeting the elderly, the technology of detecting photoplethysmogram information, which is the basic information of the bio signal and the abnormal state of the behavior pattern such as the fall frequently occurring to the elderly, can inform of an emergency with the minimum error by integrating the existing independent devices to secure more reliable results.

Korean Patent Application Nos. 1999-0041503 and 2000-0059580 propose a simple structure that detects a pulse measurable in a human body from a mobile sensor and informs medical centers or an emergency medical agency when the pulse rate exceeds the normal range.

Korean Patent Application No. 2007-0094904 proposes a method that wears the device as a watch type on a wrist and then, senses the photoplethysmogram vibration generated on a radial artery of a wrist, thereby making it possible to sense the photoplethysmogram while the user naturally carries the device. As the method for sensing the photoplethysmogram, there are a piezoelectric method, an optical method, and a non-invasive method, etc. Since the piezoelectric method senses the photoplethysmogram vibration of the radial artery, there is a problem in that it generates an air pressure to some degree in order for the sensor to support the artery. The optical method does not sense the vibration but indirectly senses a variation rate in the volume of the blood vessel of the radial artery by near-infrared absorption using near-infrared rays.

However, the distortion occurs in measuring the bio signal due to behavior noise of the user while obtaining the bio signals from the user in daily life, such that the reliability of the above-mentioned methods is degraded.

SUMMARY OF THE INVENTION

The present invention proposes to solve the problems of the related art. It is an object of the present invention to provide a method for improving reliability by supplementing the weak points of each of the technologies for sensing photoplethysmogram and fall independent from each other and combining the two independent technologies among the above-mentioned technologies.

The present invention is not limited to the above-mentioned object and other objects, which are not described above, can be obviously understood to those skilled in the art from the following description.

According to an aspect embodiment of the present invention, there is provided an apparatus and for sensing photoplethysmogram and fall, including: a sensor unit that senses acceleration and photoplethysmogram; a photoplethysmogram/fall determining module that synthetically tests sensed acceleration signals and photoplethysmogram signals sensed by the sensor unit to determine whether emergency occurs due to fall or emergency occurs due to photoplethysmogram; and a communication module that transmits the test results.

According to another aspect embodiment of the present invention, there is provided a method for sensing photoplethysmogram and fall, including: sensing acceleration signals and photoplethysmogram signals; and synthetically testing the acceleration signals and the photoplethysmogram signal to determine whether emergency occurs due to fall or emergency occurs due to photoplethysmogram.

The details of other exemplary embodiments are included in the detailed description and the drawings.

According to the exemplary embodiment of the present invention, it minimizes the user inconvenience in wearing the bio signal measuring device, improves the reliability by complementarily using the photoplethysmogram and fall, and can contribute to the commercialization and marketing for the online-based health care related technology.

BRIEF DESCRIPTION OF THE DRAWINGS

FIG. 3 is a flow chart for explaining a method for sensing photoplethysmogram and fall according to an exemplary embodiment of the present invention; and FIG. 4 is a conceptual diagram for explaining a detailed method in order a photoplethysmogram and fall determining module to determine whether ordinary behavior is conducted from an acceleration speed and whether fall occurs in a process of testing acceleration signals.

DETAILED DESCRIPTION OF THE PREFERRED EMBODIMENTS

Advantages and features of the present invention and methods to achieve them will be elucidated from exemplary embodiments described below in detail with reference to the accompanying drawings. However, the present invention is not limited to exemplary embodiment disclosed herein but will be implemented in various forms. The exemplary embodiments are provided by way of example only so that a person of ordinary skill in the art can fully understand the disclosures of the present invention and the scope of the present invention. Therefore, the present invention will be defined only by the scope of the appended claims. Meanwhile, terms used in the present invention are to explain exemplary embodiments rather than limiting the present invention. In addition, "connecting" one element to another element can be directly on another element or be indirectly on another element with one or more intervening elements interposed therebetween. In the specification, a singular type may also be used as a plural type unless stated specifically. "Comprises" and/or "comprising" used herein do not exclude the existence or addition of one or more other components.

Figure 1:
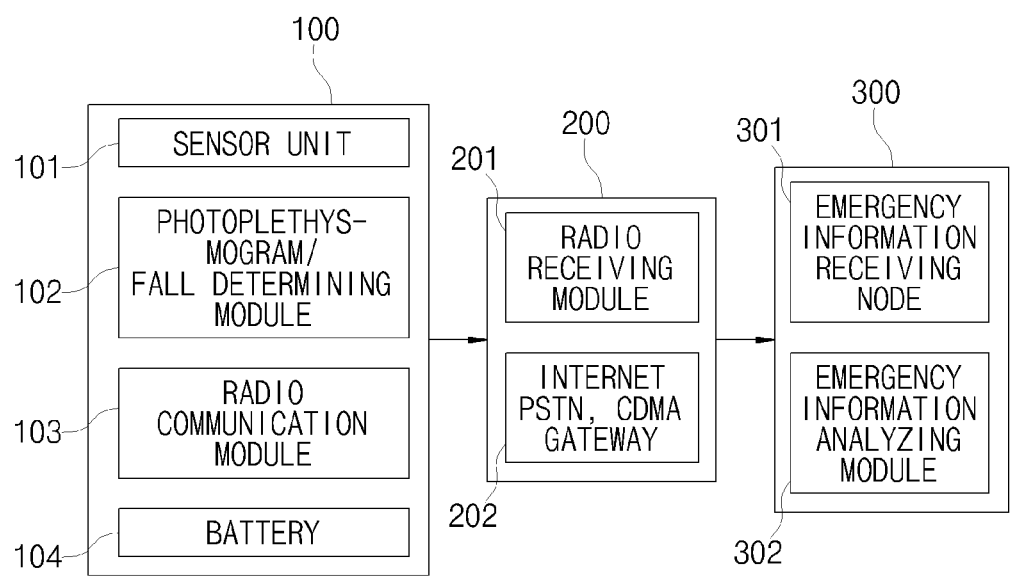
FIG. 1 is a block diagram for explaining an apparatus and a method for sensing photoplethysmogram and fall according to an exemplary embodiment of the present invention.
Figure 2:
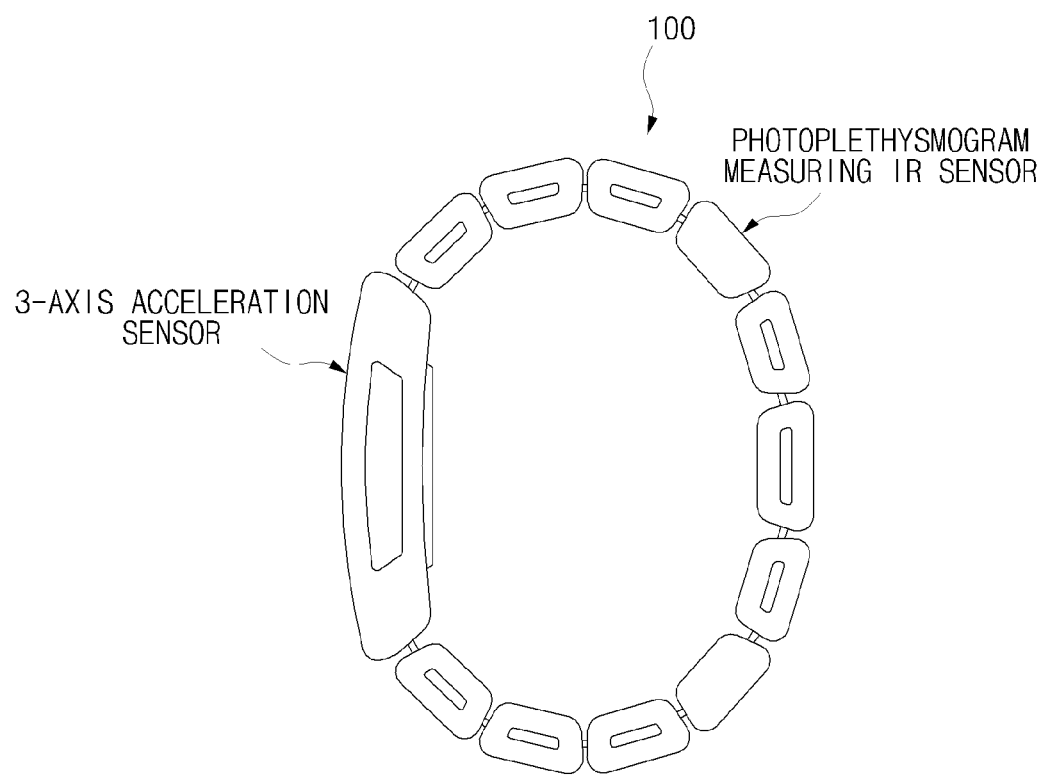
FIG. 2 is a diagram exemplarily showing a wrist wearable apparatus for sensing photoplethysmogram and fall.

FIG. 1 is a block diagram for explaining an apparatus and a method for sensing photoplethysmogram and fall according to an exemplary embodiment of the present invention, FIG. 2 is a diagram exemplarily showing a wrist wearable apparatus for sensing photoplethysmogram and fall, and FIG. 3 is a flow chart for explaining a method for sensing photoplethysmogram and fall according to an exemplary embodiment of the present invention. Hereinafter, a wrist wearable apparatus for sensing photoplethysmogram and fall will be described by way of example, but the present invention is not limited thereto.

A system for sensing photoplethysmogram and fall may be configured to include an apparatus 100 for sensing photoplethysmogram and fall, a gateway 200 that transmits information transmitted from the apparatus 100 for sensing photoplethysmogram and fall to an emergency handling related agency, and an emergency related agency 300. The apparatus 100 for sensing photoplethysmogram and fall may be built in, for example, a watch worn on the wrist of the user as shown in FIG. 2. Therefore, the apparatus 100 for sensing photoplethysmogram and fall is worn on the wrist of the user without inconveniencing the user, thereby making it possible to simultaneously sense the photoplethysmogram and fall.

The apparatus 100 for sensing photoplethysmogram and fall and the gateway 200 interfaces with the gateway 200 by a radio communication (Zigbee, Bluetooth) means and the emergency related agency 300 may interface with the gateway 200 according to wireless/wired communication protocols.

The apparatus 100 for sensing photoplethysmogram and fall may include a sensor unit 101, a photoplethysmogram/fall determining module 102, a radio communication module 103, and a battery 104.

The sensor unit 101 senses the photoplethysmogram and fall or not of the user. The sensor unit 101 may include a near-infrared LED sensing the photoplethysmogram, a pair of photodetectors for sensing the photoplethysmogram, and an MEMS 3-axis acceleration sensor for sensing fall or not.

The photoplethysmogram/fall determining module 102 pre-processes the signals sensed in the sensor unit 101, mutually supplements and synthetically tests the sensed photoplethysmogram and the sensed acceleration information by extracting features, thereby determining whether the user is in need of emergency services.

The radio communication module 103 transmits the user state information or the emergency information to the outside and the battery unit 104 supplies power to the radio communication module 103 and the photoplethysmogram/fall determining module 102.

The gateway 200 includes a radio receiving module 201 that receives information transmitted from the apparatus 100 for sensing photoplethysmogram and fall and an Internet/PSTN/CDMA gateway 202 that transmits it to the corresponding agency.

The emergency handling related agency includes a receiving node 301 and an emergency information analyzing module 302 that analyzes the received emergency information or the user state information and handles it.

Meanwhile, the photoplethysmogram and fall determining module 102 built in the apparatus 100 for sensing photoplethysmogram and fall may be included in the emergency information analyzing module 302 of the emergency handling related agency 300 according to the driving environment, differently from one shown in FIG. 1.

The operational process of the photoplethysmogram and fall determining module 102 will be described with reference to FIG. 3.

Referring to FIG. 3, the operation of the photoplethysmogram and fall determining module 102 may be largely divided into a portion determining the emergency or not according to the fall of <I> and a portion determining the emergency or not according to the photoplethysmogram of <II>. Each of the testing/analyzing results in <I> and <II> portions are mutually supplemented to synthetically determine the information of the current state, thereby determining the emergency or not.

The photoplethysmogram/fall determining module 102 stores the user state history information such as the past photoplethysmogram testing results, the fall testing results, etc., and performs the current photoplethysmogram test and fall test based on the stored information to determine the emergency or not. The state history information is stored in a frame storage unit 10 for each frame in one frame form. The number of stored frames depends on, for example, internal memory capacity of a wearable watch. The information that can be stored in one frame includes the behavior pattern of the user, the average heart rate, the fall occurrence or not, the waveform correction or not, etc., at each frame.

The process <I> of determining fall will be described based on the photoplethysmogram/fall determining module 102 using the information of the photoplethysmogram.

First, the 3-axis acceleration sensor built in the sensor unit 101 senses the acceleration of the wrist (S301) to output the acceleration signals and the photoplethysmogram/fall determining module 102 performs a pre-processing process that removes noise from the acceleration signal and removes gravity component, collects the acceleration signals in a frame size Δf unit and frames them (S302), overlaps the current frame with the next frame by Δd(<Δf), and tests the accelerations signals for each frame unit (S303).

In detail, the photoplethysmogram/fall determining module 102 analyzes the acceleration signal of the current frame period to classify whether the frame period is the fall occurring period or the ordinary behavior occurring period. For example, whether the frame period is the fall occurring period or ordinary behavior occurring period can be classified into the test results of the acceleration signal from the past. For example, the photoplethysmogram/fall determining module 102 uses experimental data or weights, etc., previously derived from many participants to analyze the acceleration signal of the current frame period and can classify whether the frame period is the fall occurring period or ordinary behavior occurring period. The detailed process will be described below with reference to FIG. 4.

If it is determined that the current frame is classified into the ordinary behavior period (S304), the ordinary behavior patterns are classified based on the acceleration signals of the current frame and the results are stored in the state frame unit 10 as the state history information (S305). For example, if it is determined that it is sensed as the ordinary behavior according to the results of analyzing the acceleration signals, the photoplethysmogram/fall determining module 102 classifies the corresponding frame into walking, running, staggering, going up and down the stairs, simple impact of hand, static behavior (for example, sitting and lying state), etc., and stores them.

If it is determined that the current frame is sensed as the falling period (S306), the photoplethysmogram/fall determining module 102 is primarily sensed as the emergency and tests whether the previous frames are in any behavior period for Δt1 prior to the current frame (S307). Since the elderly are more likely to fall while going up and down the stairs and the elderly are less likely to fall in the sitting state, it refers to the behavior of the previous frame. Alternatively, the behavior of the following frame may be referenced. In other words, the behavior of the current frame and the adjacent frames at other times may be referenced. The priority of the referenced behaviors may be previously set. For example, the priority is defined in sequence of going up and down the stairs, staggering, running, walking, and static behavior and the behavior and the priority may be searched. The priority may be said to be the sequence having high probability in determining that the current frame is emergency.

If the fall occurs, the state of the elderly may suddenly worsen due to the impact of the fall or when the elderly rise themselves and then, can conduct the normal behavior. In this case, since the emergency call due to the fall is not transmitted, the photoplethysmogram/fall determining module 102 may further test the behavior of the frame after the fall. The behavior test of the frame after the fall may be performed by referring to the classification results of step S303 for the frame during Δt2 period.

In addition, the photoplethysmogram/fall determining module 102 can use the photoplethysmogram information to supplement the tested information in order to determine the fall or not in "<1>". In other words, the photoplethysmogram/fall determining module 102 may query what the photoplethysmogram/fall signal testing results are in the previous frames during Δt1 of the frame where the fall occurs and the following frames during Δt2. The photoplethysmogram signal testing results are stored in the state frame storage unit 10 as the state history information.

The photoplethysmogram/fall determining module 102 synthetically determines the behavior testing results and the photoplethysmogram testing results of the frame before and after the fall at step S307 to determine the emergency due to the fall.

At this time, the photoplethysmogram/fall determining module 102 observes the change in heart rate from a first state histogram that does not consider the time sequence of the frames before the fall and the frames after the fall and the second state histogram considering the time sequence and can determine whether the emergency occurs from the results. Specifically, the photoplethysmogram/fall determining module 102 tests whether the variation rate in a heart rate is in the normal range and measures the range of the heart rate that is mainly distributed and the monotonous increase and monotonous reduction of a heart rate, the vibration, the variation rate in a heart rate from the first and second state histogram. The grade of the emergency may be determined as steps of caution, warning, and emergency by defining the priority of the excess of the normal range, vibration exceeding a range, vibration in a normal range, the excess of monotonous increase, the excess of monotonous reduce of heart rate, etc.

The photoplethysmogram/fall determining module 102 performs the emergency call according to the determined results (S309).

Next, the process <II> that the photoplethysmogram/fall determining module 102 analyzes and determines the photoplethysmogram using the information determining fall will be described.

The optical sensor built in the sensor unit 101, for example, the near-infrared LED and the pair of photodetectors sensing the near-infrared ray measure the photoplethysmogram of the radial artery (S310). The photoplethysmogram/fall determining module 102 estimates the behavior noise by using the pre-processing at step S302 and the filtered 3-axis acceleration signal in order to remove noise generated by the user behavior from the measured photoplethysmogram signal (S311) and filters the estimated noise and pre-processes it and frames the photoplethysmogram signal in the same Δf time period as in the acceleration signal (S312). The photoplethysmogram/fall determining module 102 tests the photoplethysmogram signal of the current frame (S313).

Specifically, the photoplethysmogram/fall determining module 102 measures a distortion measurement, the periodicity test, an amplitude size of the photoplethysmogram signal, power of a low frequency band, etc., from the photoplethysmogram signal to classify whether the current frame is in a normal period or not.

If it is determined that the current frame is classified into the normal period (S314), the photoplethysmogram/fall determining module 102 determines the state of a heart rate in the current frame period through the analysis of the current heart rate, the test of a normal range, and the analysis of variation rate in a heart rate and stores the photoplethysmogram test results (S315).

If it is determined that the current frame is classified into the abnormal period (S316), the photoplethysmogram/fall determining module 102 queries what the behavior pattern according to the acceleration of the current frame (or previous frame, post frame) is (S317). At this time, the priority is set according to the kind of behavior pattern, for example, the behavior pattern such as going up and down the stairs, running, etc., which can determine whether the factors increasing the current heart rate is due to the abnormality of body or due to an ordinary behavior or behavior pattern increasing the heart rate in consideration of the priority of the behavior patterns queried at step S317.

Further, since the purpose of measuring the photoplethysmogram is to monitor the state information of the elderly, it is important to know the current state as well as what the state is changed for a period to some degree before the present and how long the state exceeding the normal range is continued. Therefore, the results tested in the current frame are stored in the state frame storage unit 10 as the state history information. However, since indefinitely dividing and analyzing the time period is inefficient in terms of accuracy or calculation, the photoplethysmogram/fall determining module 102 queries the behavior patterns of the frames at other times adjacent to the current frame, for example, the frames in the past five minutes (Δt1) to synthetically analyze the past behavior pattern and the current behavior pattern, thereby making it possible to determine the emergency (S318). If an emergency occurs, an emergency call is performed (S309).

FIG. 4 shows in detail a previously performed process and a detailed method of step S303 in order for the photoplethysmogram/fall determining module 102 to determine whether the user conducts the ordinary behavior or whether the user falls from the acceleration signals at step S303 for testing the acceleration signal of FIG. 3.

The flow shown in FIG. 4 obtains a large amount of data such as various behaviors previously obtained from many participants, for example, walking, running, going up and down the stairs, falling, etc., and provides a pattern dividing boundary line that can well divide the fall pattern and the ordinary behavior pattern with the lowest error rate by using a teacher learning method. The obtained pattern dividing boundary line is formed to include several weights, wherein the weight is used to determine whether the user conducts an ordinary behavior or falls from the acceleration signals at step S303 of testing the acceleration signals of FIG. 3 by the photoplethysmogram/fall determining module 102 in FIG. 3.

In detail, referring to FIG. 4, after it performs the preprocessing filtering in order to remove noise and gravity component from the acceleration signals of many participants stored in an acceleration pattern DB 50, it collects and frames the acceleration signals for the Δf period (51) and extracts features owned by the patterns of the acceleration signals of each frame and performs the feature-vector thereon (52). At this time, since the order of the vector is generally large, it reduces the dimension of the feature vector to the minimum dimension without losing the specific information in order to reduce computations (53). If the dimensional reduced feature vectors are input to a fall pattern classifier 54 provided in the photoplethysmogram/fall determining module 102, the photoplethysmogram/fall determining module 102 can classify whether they are in the fall occurring period or the ordinary behavior occurring period by using the foregoing weights The results classified at the current step are again stored in the acceleration pattern DB (50) and may be used to update the pattern dividing boundary line and several weights. In other words, the test results at step S303 are reflected to the pattern dividing boundary line or several weights and the photoplethysmogram/fall determining module 102 can classify whether the current frame is in the fall occurring period or the ordinary behavior occurring period by using newly updated pattern dividing boundary line or several weights.

While certain embodiments have been described above, it will be understood to those skilled in the art that the embodiments described can be modified into various forms without changing the technical spirit or essential features. Accordingly, the embodiments described herein are provided by way of example only and should not be construed as being limited. While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. An apparatus for sensing photoplethysmogram and fall comprising:
   a sensor unit that senses acceleration and photoplethysmogram;
   a photoplethysmogram/fall determining module that synthetically tests the acceleration signals and photoplethysmogram signals sensed by the sensor unit to determine whether an emergency occurs due to fall or an emergency occurs due to photoplethysmogram; and
   a communication module that transmits the determined results,
   wherein the photoplethysmogram/fall determining module,
      collects and frames the acceleration signals and the photoplethysmogram signals and tests and determines the acceleration signals and the photoplethysmogram signals in a frame unit,
      tests the acceleration signals for one frame to decide whether the user conducts ordinary behavior or falls, and
      classifies and stores the behavior pattern from the acceleration signals of one frame if it is determined that the user conducts ordinary behavior according to the test results.

2. The apparatus for sensing photoplethysmogram and fall according to claim 1, wherein the photoplethysmogram/fall determining module estimates noise generated due to the motion of the user by using the acceleration signals and removes the estimated noise from the photoplethysmogram signals.

3. The apparatus for sensing photoplethysmogram and fall according to claim 1, wherein the photoplethysmogram/fall determining module decides the normal photoplethysmogram or not by testing the photoplethysmogram signals for one frame.

4. The apparatus for sensing photoplethysmogram and fall according to claim 3, wherein the photoplethysmogram/fall determining module tests and stores the state of heart rate from the photoplethysmogram signals of one frame if it is determined that it is normal photoplethysmogram according to the test results.

5. The apparatus for sensing photoplethysmogram and fall according to claim 3, wherein the photoplethysmogram/fall determining module queries the behavior patterns classified from the acceleration signals of at least one frame at other times adjacent to the frame to determine the emergency according to the photoplethysmogram, if it is determined that it is abnormal according to the test results.

6. The apparatus for sensing photoplethysmogram and fall according to claim 1, wherein the apparatus for sensing photoplethysmogram and fall is worn on the body of the user.

7. The apparatus for sensing photoplethysmogram and fall according to claim 1, wherein the communication module transmits the emergency due to the fall or the emergency due to the photoplethysmogram to an emergency related agency through a gateway.

8. An apparatus for sensing photoplethysmogram and fall, comprising:
   a sensor unit that senses acceleration and photoplethysmogram;
   a photoplethysmogram/fall determining module that synthetically tests the acceleration signals and photoplethysmogram signals sensed by the sensor unit to determine whether an emergency occurs due to fall or an emergency occurs due to photoplethysmogram; and
   a communication module that transmits the determined results,
   wherein the photoplethysmogram/fall determining module,
      collects and frames the acceleration signals and the photoplethysmogram signals and tests and determines the acceleration signals and the photoplethysmogram signals in a frame unit,
      tests the acceleration signals for one frame to decide whether the user conducts ordinary behavior or falls, and
      queries the behavior pattern classified from acceleration signals of at least one frame at other times adjacent to the frame and the test results of the photoplethysmogram signal to determine the emergency due to the fall, if it is determined that the user falls according to the test results.

9. The apparatus for sensing photoplethysmogram and fall according to claim 8, wherein the photoplethysmogram/fall determining module estimates noise generated due to the motion of the user by using the acceleration signals and removes the estimated noise from the photoplethysmogram signals.

10. The apparatus for sensing photoplethysmogram and fall according to claim 8, wherein the photoplethysmogram/fall determining module decides the normal photoplethysmogram or not by testing the photoplethysmogram signals for one frame.

11. The apparatus for sensing photoplethysmogram and fall according to claim 8, wherein the apparatus for sensing photoplethysmogram and fall is worn on the body of the user.

12. The apparatus for sensing photoplethysmogram and fall according to claim 8, wherein the photoplethysmogram/fall determining module tests and stores the state of heart rate from the photoplethysmogram signals of one frame if it is determined that it is normal photoplethysmogram according to the test results.

13. The apparatus for sensing photoplethysmogram and fall according to claim 8, wherein the photoplethysmogram/fall determining module queries the behavior patterns classified from the acceleration signals of at least one frame at other times adjacent to the frame to determine the emergency according to the photoplethysmogram, if it is determined that it is abnormal according to the test results.

14. The apparatus for sensing photoplethysmogram and fall according to claim 8, wherein the communication module transmits the emergency due to the fall or the emergency due to the photoplethysmogram to an emergency related agency through a gateway.

15. A method for sensing photoplethysmogram and fall, comprising:
   sensing acceleration signals and photoplethysmogram signals;
   synthetically testing the acceleration signals and the photoplethysmogram to determine whether an emergency occurs due to fall or emergency occurs due to photoplethysmogram;
   collecting and testing the acceleration signals for one frame; and
   deciding whether one frame is in an ordinary life period or a fall period according to the test results,
   wherein the determining further includes classifying and storing the behavior pattern from the acceleration signals of one frame if it is determined that the user conducts ordinary behavior according to the test results.

16. The method for sensing photoplethysmogram and fall according to claim 15, wherein the determining further includes querying the behavior pattern classified from acceleration signals of at least one frame at other times adjacent to the frame and the test results of the photoplethysmogram signal to determine the emergency due to the fall, if it is determined that the user falls according to the test results.

17. The method for sensing photoplethysmogram and fall according to claim 15, wherein the determining includes,
   estimating noise generated due to the motion of the user by using the acceleration signals;
   removing the estimated noise from the photoplethysmogram signals; and
   deciding the normal photoplethysmogram or not by testing the photoplethysmogram signals in which noise is removed.

18. The method for sensing photoplethysmogram and fall according to claim 17, wherein the determining tests and stores the state of heart rate from the photoplethysmogram signals of one frame if it is determined that it is normal photoplethysmogram according to the test results.

19. The method for sensing photoplethysmogram and fall according to claim 17, wherein the determining queries the behavior patterns classified from the acceleration signals of at least one frame at other times adjacent to the frame to determine the emergency according to the photoplethysmogram, if it is determined that it is abnormal according to the test results.

20. The method for sensing photoplethysmogram and fall according to claim 15, further comprising transmitting the emergency due to the fall or the emergency due to the photoplethysmogram to an emergency related agency through a gateway.

* * * * *